United States Patent
Nakamura et al.

(10) Patent No.: US 9,921,130 B2
(45) Date of Patent: Mar. 20, 2018

(54) FATIGUE TESTING DEVICE

(71) Applicant: NISSHIN STEEL CO., LTD., Tokyo (JP)

(72) Inventors: Sadayuki Nakamura, Tokyo (JP); Hiroyasu Matsubayashi, Tokyo (JP); Akira Hironaka, Tokyo (JP); Ryoji Hirota, Tokyo (JP)

(73) Assignee: Nisshin Steel Co., LTD., Tokyo (JP)

( * ) Notice: Subject to any disclaimer, the term of this patent is extended or adjusted under 35 U.S.C. 154(b) by 201 days.

(21) Appl. No.: 14/780,174

(22) PCT Filed: Mar. 4, 2014

(86) PCT No.: PCT/JP2014/055445
§ 371 (c)(1),
(2) Date: Sep. 25, 2015

(87) PCT Pub. No.: WO2014/156510
PCT Pub. Date: Oct. 2, 2014

(65) Prior Publication Data
US 2016/0033357 A1    Feb. 4, 2016

(30) Foreign Application Priority Data

Mar. 27, 2013    (JP) .................... 2013-066292

(51) Int. Cl.
*G01N 3/32*    (2006.01)
*G01N 3/36*    (2006.01)
*G01M 7/02*    (2006.01)

(52) U.S. Cl.
CPC .............. *G01M 7/027* (2013.01); *G01N 3/32* (2013.01); *G01N 3/36* (2013.01);
(Continued)

(58) Field of Classification Search
CPC .... G01N 3/32; G01N 3/36; G01N 2203/0005; G01N 2203/0044; G01N 2203/04; G01N 2203/0282; G01M 7/027
(Continued)

(56) References Cited

U.S. PATENT DOCUMENTS

| | | | |
|---|---|---|---|
| 2,171,303 A | 8/1939 | De Forest | |
| 2,373,351 A | 4/1945 | Sims, Jr. | |
| 3,023,610 A * | 3/1962 | Prochazka | ............... G01N 3/38 |
| | | | 73/578 |

FOREIGN PATENT DOCUMENTS

| | | |
|---|---|---|
| GB | 632596 A | 11/1949 |
| GB | 1017099 A | 1/1966 |

(Continued)

OTHER PUBLICATIONS

Supplementary European Search Report cited in European Application 14772836 dated Oct. 20, 2016, 9 pages.
(Continued)

*Primary Examiner* — J M Saint Surin
(74) *Attorney, Agent, or Firm* — Rothwell, Figg, Ernst & Manbeck, P.C.

(57) ABSTRACT

A fatigue testing device 1 comprises a fixing member 4 constituted by a lower jig 2 and an upper jig 3. The lower jig 2 and the upper jig 3 are fixed with a bolt 5, and a sheet or plate-shaped metal plate 6 is fixed in a cantilever state such that it is interposed between the lower jig 2 and the upper jig 3. The lower jig 2 has a fixing surface 2a to which the metal sheet or plate 6 is fixed, and the fixing surface 2a has a curved shape such that the space between the fixing surface 2a and the metal sheet or plate 6 increases with increasing distance from the location where the metal sheet or plate 6 is fixed to the fixing surface 2a. The upper jig 3 also has a fixing surface 3a to which the metal sheet or plate 6 is fixed, and the fixing surface 3a has a curved shape such that the space between the fixing surface 3a and the metal sheet or plate 6 increases with increasing distance from the location where the metal sheet or plate 6 is fixed to the fixing surface 3a.

6 Claims, 3 Drawing Sheets

(52) U.S. Cl.
    CPC ............... *G01N 2203/0005* (2013.01); *G01N 2203/0044* (2013.01); *G01N 2203/0282* (2013.01); *G01N 2203/04* (2013.01)

(58) Field of Classification Search
    USPC .......................................................... 73/577
    See application file for complete search history.

(56) References Cited

FOREIGN PATENT DOCUMENTS

| | | | |
|---|---|---|---|
| JP | 5425786 A | | 2/1979 |
| JP | 2003042917 | * | 2/2003 |
| JP | 2004077163 A | | 3/2004 |
| JP | 2008-203092 A | | 9/2008 |
| JP | 2012-149979 A | | 8/2012 |
| JP | 2014066603 | * | 4/2014 |
| SU | 1727035 | * | 4/1992 |
| WO | 2009112795 A2 | | 9/2009 |

OTHER PUBLICATIONS

International Search Report issued in PCT Appln. No. PCT/JP2014/055445 dated Apr. 15, 2014, 1 page.
Office Action issued in Japanese Patent Appln. No. 2013-066292 dated Jul. 14, 2015 along with English translation, 4 pages.

* cited by examiner

FATIGUE TESTING DEVICE

CROSS REFERENCE TO RELATED APPLICATIONS

This application is a 35 U.S.C. § 371 National Phase Entry Application from PCT/JP2014/055445, filed on Mar. 4, 2014, and designating the United States, which claims priority under 35 U.S.C. § 119 to Japanese Patent Application No. 2013-066292 filed on Mar. 27, 2013, which is incorporated herein by reference in its entirety.

TECHNICAL FIELD

The present invention relates to a fatigue testing device, and more particularly to a fatigue testing device for grasping a fatigue life of sheet or plate-shaped products made of metal, glass, ceramics, or the like.

BACKGROUND ART

In transportation equipment such as automobiles and airplanes, and in industrial machinery or the like, stress is repeatedly loaded onto materials used therein by vibration and repeated driving. Therefore, it is important to grasp the fatigue life of the materials to be used, and fatigue tests are typically performed.

In conventional fatigue tests, the life is typically predicted using a load of $1 \times 10^7$ repeated loading. In recent years, however, there have been demands for transportation equipment and industrial machinery with extended service lives. As a result of a variety of research, for example, in metals, $1 \times 10^9$ repeated loading have been evaluated as a fatigue limit stress in view of the effect of metallic inclusions present in the metals.

The conventional fatigue tests are generally classified into tension-compression stress types, bending stress types, and torsional stress types. In a tension-compression stress type fatigue test which is performed with a test piece in the form of a round rod or the like, there are fatigue testing machines capable of high-speed loading by hydraulic drive, or the like, in addition to mechanical drive, and depending on the stress, high-speed tests at or above 1000 Hz can be performed. A high-speed fatigue testing device using an ultrasound oscillator has recently been developed, and such a device is suitable for giga-cycle fatigue tests. However, if a test frequency is increased in such fatigue testing devices, heat generation may occur due to strains in the test piece, and a test piece cooling system or the like is also needed.

Meanwhile, since the fatigue testing of tension-compression stress types and torsional stress types are difficult to perform with respect to sheet or plate-shaped test pieces, fatigue testing of bending stress types is typically performed. A completely reversed fatigue test in which a crank is connected to a rotating body and both ends of a test piece are mechanically bent and a fatigue test in which one end of a test piece is fixed and the end on the opposite side is mechanically vibrated are typically used to load bending stress onto a sheet or plate-shaped test piece. Therefore, since the test frequency is restricted by the rotational speed of the drive motor or the like and the heat generation preventing ability, 1800 spm is the limit, about 2 to 5 days are required to load $1 \times 10^7$ repeated stress, and the number of days which is larger by a factor of 100 is further required to load $1 \times 10^9$ repeated stress. Furthermore, a detector such as a high-precision load cell is required to detect the decrease in stress resulting from the occurrence of fatigue cracks, and so the cost of the fatigue testing device increases accordingly.

On the contrary, Patent Document 1 describes a fatigue testing device which can easily perform a giga-cycle fatigue test in a short period of time. In the fatigue test performed with this fatigue testing device, a test piece which is fixed at a proximal end side with a fixing jig is vibrated by applying a pulsed pressure wave generated from a pulse generator driven by a high-frequency motor. In this case, the vibration frequency of the test piece becomes a resonance frequency by adjusting the frequency of pressure variations in the pressure wave so as to match the resonance frequency of the test piece.

Patent Document 1: Japanese Patent Application Laid Open No. 2012-149979.

SUMMARY OF THE INVENTION

However, in the fatigue testing device described in Patent Document 1, the test piece is caused to vibrate while only the proximal end side of the test piece is fixed to the fixing jig. Thus, there is a problem in that when the vibration frequency of the test piece is not adjusted appropriately, the amplitude of test piece vibrations becomes too large, large stress is applied, and the test piece may be fractured.

The present invention has been designed to resolve this problem, and it is an objective of the present invention to provide a fatigue testing device that can prevent unnecessarily large stress from being applied to the test piece.

The fatigue testing device of the present invention is a fatigue testing device for testing the fatigue life of a test piece by having the test piece vibrate, the fatigue testing device comprising: a first fixing jig which has a first fixing surface to which the test piece is fixed in a cantilever state; a vibrator which causes the test piece to vibrate by blowing compressed gas in a pulse form onto the test piece; and a displacement detector which detects a vibration displacement of the test piece, wherein the test piece is fixed to the first fixing surface such that a space is present between the test piece and the first fixing surface at least at a location that is other than the location where the test piece is fixed.

According to the present invention, by fixing the test piece to the first fixing surface in a manner such that a space is present between the test piece and the first fixing surface at least at a location that is other than the location where the test piece is fixed, it is possible to suppress the vibrations of the test piece with the first fixing surface even in the case of an excessively large amplitude of vibrations of the test piece when the test piece vibrates. Therefore, unnecessarily large stress can be prevented from being applied to the test piece.

DESCRIPTION OF THE EMBODIMENT

An embodiment of the present invention will be explained hereinbelow with reference to the appended drawings.

Figure 1:
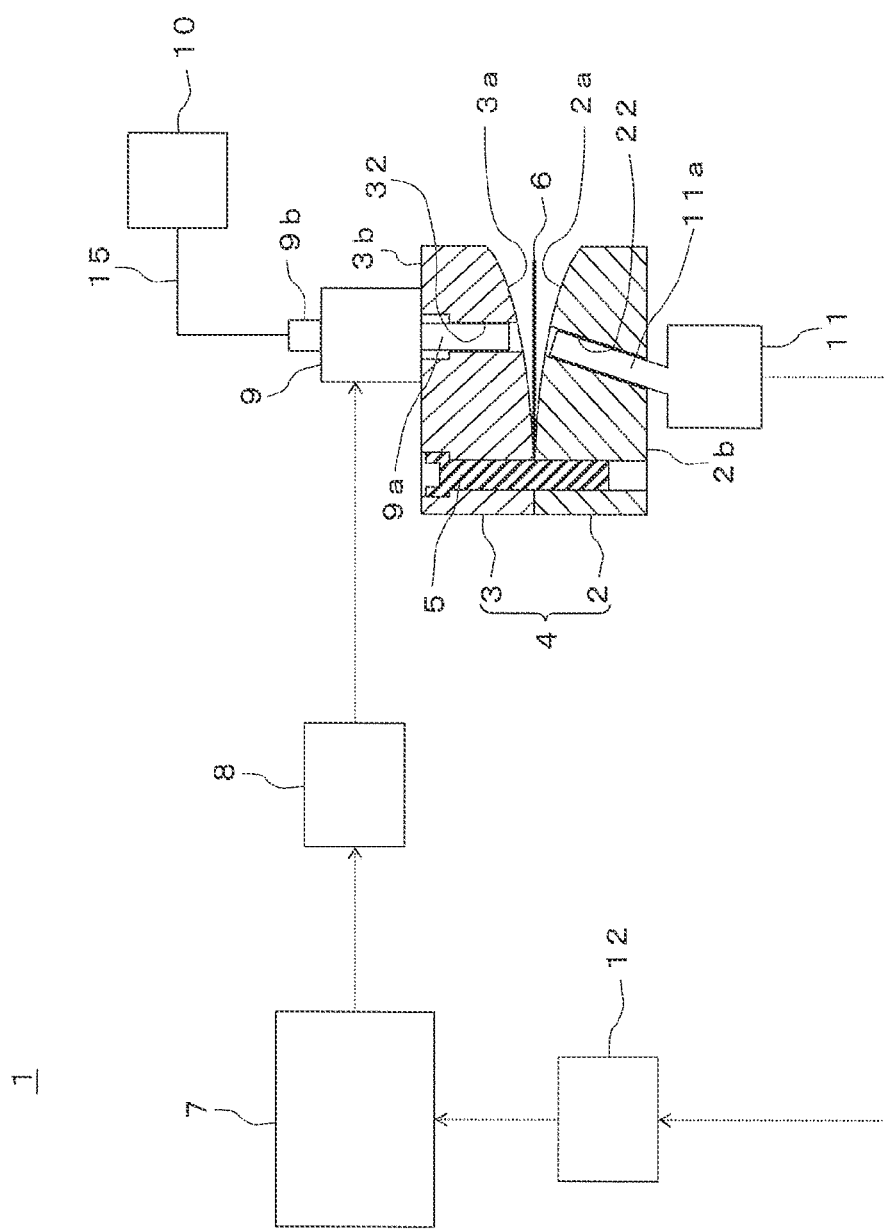
FIG. 1 is a schematic diagram illustrating the configuration of the fatigue testing device according to an embodiment of the present invention.

As shown in FIG. 1, a fatigue testing device 1 comprises a fixing member 4 constituted by a lower jig 2 which is a first fixing jig, and an upper jig 3 which is a second fixing jig. The lower jig 2 and the upper jig 3 are fixed with a bolt 5, and a sheet or plate-shaped metal plate 6 which is a test piece is fixed in a cantilever state such that it is interposed between the lower jig 2 and the upper jig 3.

The lower jig 2 has a fixing surface 2a (first fixing surface) to which the metal plate 6 is fixed, and the fixing surface 2a has a curved shape such that the space between the fixing surface 2a and the metal plate 6 increases with increasing distance from the location where the metal plate 6 is fixed to the fixing surface 2a. The upper jig 3 also has a fixing surface 3a (second fixing surface) to which the metal plate 6 is fixed, and the fixing surface 3a has a curved shape such that the space between the fixing surface 3a and the metal plate 6 increases with increasing distance from the location where the metal plate 6 is fixed to the fixing surface 3a. The end of the metal plate 6 which is not fixed is positioned between the fixing surfaces 2a and 3a.

Figure 2:
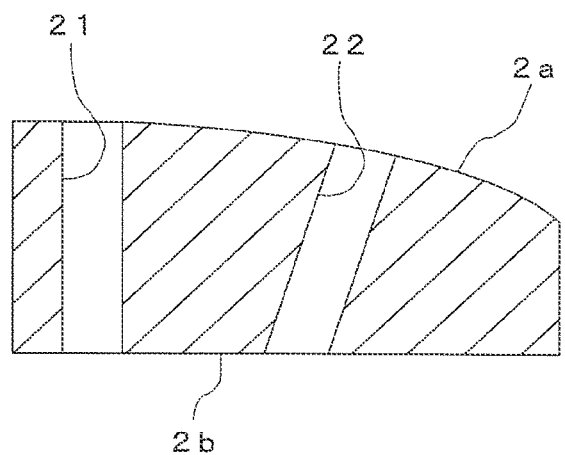
FIG. 2 is a cross-sectional view of the lower jig of the fatigue testing device according to the embodiment.

As shown in FIG. 2, the lower jig 2 has a bottom surface 2b substantially facing the fixing surface 2a. A fixing hole 21 into which a bolt 5 is inserted (see FIG. 1) and a detection hole 22 (first through hole) into which a sensor portion 11a (see FIG. 1) of a proximity sensor 11, which will be described later, is inserted are formed in the lower jig 2 so as to pass through the lower jig 2 from the bottom surface 2b to the fixing surface 2a. The fixing hole 21 is perpendicular to the bottom surface 2b. The detection hole 22 is inclined with respect to the fixing hole 21 at an angle such that the detection hole 22 is approximately perpendicular to the fixing surface 2a in the vicinity of the fixing surface 2a.

Figure 3:
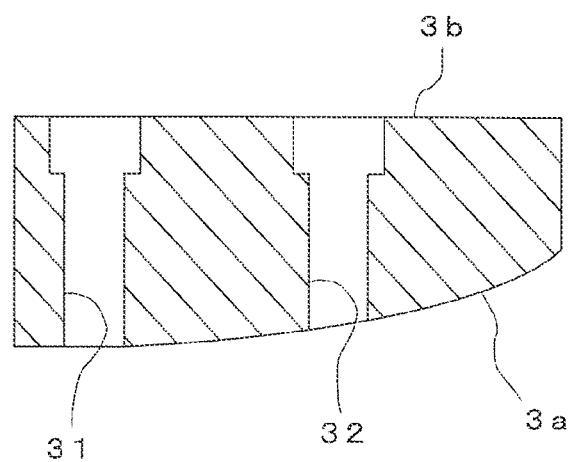
FIG. 3 is a cross-sectional view of the upper jig of the fatigue testing device according to the embodiment.

As shown in FIG. 3, the upper jig 3 has an upper surface 3b substantially facing the fixing surface 3a. A fixing hole 31 into which the bolt 5 is inserted (see FIG. 1) and an air supply hole 32 (second through hole) into which a discharge nozzle 9a (see FIG. 1) of a high-speed air valve 9, which will be described later, is inserted are formed in the upper jig 3 so as to pass through the upper jig 3 from the upper surface 3b to the fixing surface 3a. The fixing hole 31 and the air supply hole 32 are each perpendicular to the upper surface 3b.

As shown in FIG. 1, the discharge nozzle 9a of the high-speed air valve 9 is inserted into the air supply hole 32 of the upper jig 3 from the upper surface 3b side. One end of an air supply pipe 15 is connected to a supply nozzle 9b of the high-speed air valve 9, and a compressor 10 is connected to the other end of the air supply pipe 15. A signal power level conversion interface 8 is electrically connected to the high-speed air valve 9, and a function generator 7 is electrically connected to the signal power level conversion interface 8. The function generator 7, the signal power level conversion interface 8, the high-speed air valve 9, and the compressor 10 cause the metal plate 6 to vibrate by the operation which will be described later, and therefore these constitute a vibrator that causes the metal plate 6 to vibrate.

The sensor portion 11a of the proximity sensor 11 which is a displacement detector is inserted into the detection hole 22 of the lower jig 2 from the bottom surface 2b side. A counter 12 is electrically connected to the proximity sensor 11, and the counter 12 is also electrically connected to the function generator 7.

Figure 4:
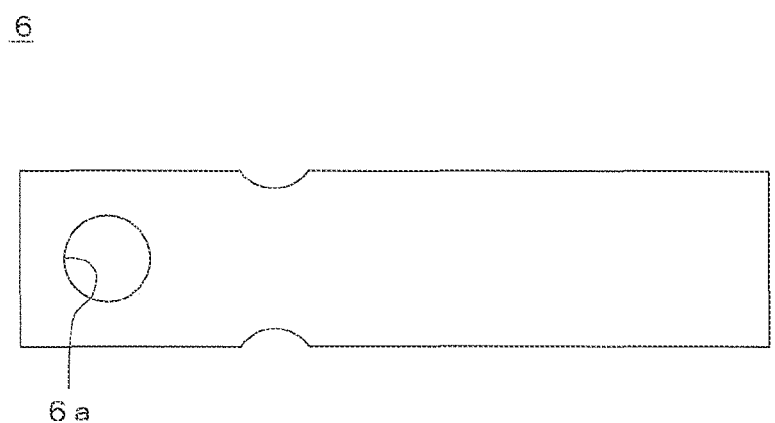
FIG. 4 is a plan view of the test piece which is tested with the fatigue testing device according to the embodiment.

As shown in FIG. 4, the metal plate 6 has a substantially rectangular thin sheet or plate-shaped form, and a fixing orifice 6a through which the bolt 5 is inserted (see FIG. 1) is formed at one end side in the longitudinal direction thereof. For example, the metal plate 6 may have the following dimensions: the length in the longitudinal direction is 45 mm; the width is 10 mm; and the thickness is 0.35 mm.

A method for fatigue testing using the fatigue testing device according to the present embodiment is described hereinbelow.

As shown in FIG. 1, a pulse wave of a predetermined frequency is generated with the function generator 7, this pulse wave is converted into the operation signal of the high-speed air valve 9 with the signal power level conversion interface 8, and a valve (not shown) provided inside the high-speed air valve 9 is periodically caused to open and close. Further, the compressor 10 sucks the air and supplies the compressed air from the supply nozzle 9b to the high-speed air valve 9 through the air supply pipe 15. The compressed air supplied to the high-speed air valve 9 is periodically discharged from the discharge nozzle 9a in response to the opening-closing operation of the valve provided inside the high-speed air valve 9. The compressed air periodically discharged from the discharge nozzle 9a is blown onto the metal plate 6 through the air supply hole 32.

When the compressed air is blown onto the metal plate 6, the end of the metal plate 6 on the side opposite to the side of the portion where the metal plate 6 is fixed between the fixing surfaces 2a, 3a is bent toward the fixing surface 2a. In this case, even if the force of the compressed air that bends the metal plate 6 is large, the maximum bending of the entire metal plate 6 is restricted by contact with the fixing surface 2a, and further bending is inhibited. After the metal plate 6 bends toward the fixing surface 2a, the metal plate 6 returns toward the fixing surface 3a due to the elasticity of the metal plate 6 itself. The maximum bending of the entire metal plate 6 in this case is also limited by contact with the fixing surface 3a, and further bending is inhibited. Therefore, no unnecessarily large stress is applied to the metal plate 6. The metal plate 6 then again bends toward the fixing surface 2a, but when the compressed air is again blown onto the metal plate 6, the metal plate 6 repeats the abovementioned operations and thus vibrates between the fixing surfaces 2a, 3a.

While the metal plate 6 vibrates in such a manner, the proximity sensor 11 detects the approach/withdrawal of the metal plate 6 to/from the fixing surface 2a, that is, the vibration displacement of the metal plate 6 through the detection hole 22. The number of bending cycles of the metal plate 6 can be detected by counting the number of approaches/withdrawals with the counter 12.

If a fatigue crack appears in the metal plate 6, the force returning the metal plate 6 toward the fixing surface 3a by the elasticity of the metal plate 6 itself after the metal plate 6 bends toward the fixing surface 2a will be weakened, thereby significantly changing the vibrations of the metal plate 6. For example, if the fatigue crack is large, the metal plate 6 will not be more or less returned toward the fixing surface 3a. As a result, the count by the counter 12 is stopped. When the stop of the count by the counter 12 is detected by the function generator 7, the function generator 7 stops generating the pulse wave and then stops the opening-closing operation of the valve of the high-speed air valve 9 and the operation of the compressor 10, thereby ending the fatigue test performed by the fatigue testing device 1. The number of bending cycles before the fatigue crack appears in the metal plate 6 can be determined from the count of the counter 12 at the time the fatigue test is ended.

Thus, by fixing the metal plate 6 to the fixing surface 2a in a manner such that a space is present between the metal plate 6 and the fixing surface 2a at least at a location that is other than the location where the metal plate 6 is fixed, it is possible to suppress the vibrations of the metal plate 6 with the fixing surface 2a even in the case of an excessively large amplitude of vibrations of the metal plate 6 when the metal plate 6 vibrates. Therefore, unnecessarily large stresses can be prevented from being applied to the metal plate 6.

In this embodiment, the metal plate 6 is fixed so as to be interposed between the lower jig 2 and the upper jig 3, but it is not limited to such a configuration. A configuration may be used in which the upper jig 3 is not present and the metal plate 6 is fixed in a cantilever state on the fixing surface 2a of the lower jig 2. Further, when the upper jig 3 is not present, the lower jig 2 is not limited to an arrangement where the fixing surface 2a faces vertically upward, but the lower jig 2 may be arranged such that the fixing surface 2a faces vertically downward or in the horizontal direction.

In this embodiment, the fixing surfaces 2a, 3a have curved shapes such that the spaces between the surfaces and the metal sheet or plate 6 increase with increasing distance from the location where the metal plate 6 is fixed, but it is not limited to such a configuration. The fixing surfaces 2a, 3a may have any shape if the spaces are formed such that the metal plate 6 can vibrate between the fixing surfaces 2a, 3a at a location that is other than the location where the metal sheet or plate 6 is fixed.

In this embodiment, the test piece is the metal plate 6 made of aluminum, stainless steel, or the like, but the test piece is not limited to a test piece made of metal. The test piece may be made of any material such as glass and ceramics if it has a plate shape.

The invention claimed is:

1. A fatigue testing device for testing fatigue life of a test piece by having the test piece vibrate, the fatigue testing device comprising:
 a first fixing jig which has a first fixing surface configured to fix thereto the test piece in a cantilever state;
 a second fixing jig configured to fix the test piece such that the test piece is interposed between the first fixing jig and the second fixing jig;
 a vibrator configured to cause the test piece to vibrate by blowing compressed gas in a pulse form onto the test piece; and
 a displacement detector configured to detect a vibration displacement of the test piece,
 wherein the second fixing jig has a second fixing surface configured to fix the test piece in a cantilever state between the first fixing surface and the second fixing surface, and
 wherein each of the first fixing surface and the second fixing surface has a location for fixing the test piece in a cantilever state, and has a shape such that, in the presence of the test piece, a space is present between the test piece and each of the first fixing surface and the second fixing surface at least at a location that is other than the location for fixing the test piece.

2. The fatigue testing device according to claim 1, wherein the first fixing surface has a curved shape such that, in presence of the test piece, the space between the first fixing surface and the test piece increases with increasing distance from the location for fixation of the test piece.

3. The fatigue testing device according to claim 1,
 wherein a first through hole that opens at the first fixing surface is provided in the first fixing jig, and
 wherein the displacement detector in configured to detect the vibration displacement of the test piece through the first through hole.

4. The fatigue testing device according to claim 1, wherein the second fixing surface has a curved shape such that, in presence of the test piece, the space between the second fixing surface and the test piece increases with increasing distance from the location for fixation of the test piece.

5. The fatigue testing device according to claim 1,
 wherein a second through hole that opens at the second fixing surface is provided in the second fixing jig, and
 wherein the vibrator is configured to cause compressed gas to be blown onto the test piece through the second through hole.

6. The fatigue testing device according to claim 1, wherein the test piece has a sheet or plate shape.

* * * * *